US007934853B2

(12) United States Patent
Coombs et al.

(10) Patent No.: US 7,934,853 B2
(45) Date of Patent: May 3, 2011

(54) MOBILE IMAGING SYSTEM WITH ADJUSTABLE LIGHT SOURCE

(75) Inventors: Kevin A Coombs, Pewaukee, WI (US); Jonathan M Butzine, Oconomowoc, WI (US)

(73) Assignee: General Electric Company, Schenectady, NY (US)

( * ) Notice: Subject to any disclaimer, the term of this patent is extended or adjusted under 35 U.S.C. 154(b) by 246 days.

(21) Appl. No.: 11/839,499

(22) Filed: Aug. 15, 2007

(65) Prior Publication Data
US 2009/0046463 A1    Feb. 19, 2009

(51) Int. Cl.
*F21V 33/00* (2006.01)
*F21V 23/04* (2006.01)
*H05G 1/00* (2006.01)

(52) U.S. Cl. .................... 362/253; 362/276; 378/204

(58) Field of Classification Search .................. 362/276, 362/802, 253, 545, 89, 485, 486; 378/204
See application file for complete search history.

(56) References Cited

U.S. PATENT DOCUMENTS

| 6,427,581 | B1 * | 8/2002 | Wu ................................ 99/332 |
| 6,844,824 | B2 * | 1/2005 | Vukosic .................... 340/815.65 |
| 6,862,472 | B2 * | 3/2005 | Mikula et al. ................. 600/523 |
| 7,046,764 | B1 * | 5/2006 | Kump ........................... 378/117 |
| 7,088,222 | B1 * | 8/2006 | Dueker et al. ................ 340/321 |
| 7,425,088 | B2 * | 9/2008 | Weitzel .......................... 362/540 |
| 2004/0230247 | A1 * | 11/2004 | Stein et al. ....................... 607/32 |
| 2007/0159817 | A1 * | 7/2007 | Evans et al. .................... 362/191 |

* cited by examiner

*Primary Examiner* — Jong-Suk (James) Lee
*Assistant Examiner* — David R Crowe
(74) *Attorney, Agent, or Firm* — William Baxter, Esq.; Michael G. Smith, Esq.; Ellis Ramirez, Esq.

(57) ABSTRACT

Systems, methods and apparatus for illuminating a mobile imaging system by use of a light source operable to emit light for status indication, pathway illumination, and/or creation of favorable lighting environment. A triggering signal originating from a photosensor arranged to receive light at the mobile imaging system, a signal indicative of movement of the mobile imaging system, or user or system command is used to adjust the lighting source. The light source can be a light emitting diode (LED), collimator lamp, halogen lamp, fluorescent lamp, organic display, or any other light-emitting technology. The light source is adjustable as to color and intensity and can indicate the mobile imaging system's condition, status, or event.

22 Claims, 7 Drawing Sheets

MOBILE IMAGING SYSTEM WITH ADJUSTABLE LIGHT SOURCE

FIELD OF THE INVENTION

The present invention relates to a mobile imaging system and more particularly to a mobile imaging system having adjustable lighting for providing status indication, pathway illumination, and creating a favorable lighting environment.

BACKGROUND OF THE INVENTION

Mobile and stationary X-ray devices are often equipped with displays, such as dedicated liquid crystal display (LCD) screens, dedicated vacuum fluorescent display (VFD) screens, cathode ray tube (CRT) monitors, or LCD monitors. These displays provide the user with system status information. In addition to operating the equipment, an X-ray technologist is required to interact with the patient. When the technologist moves away from the system display to assist the patient, he or she is no longer aware of the status of the system.

Mobile X-ray devices are used when traditional stationary radiographic systems would be difficult or impossible for a patient to utilize. They are often used in the emergency room (ER), intensive care unit (ICU), surgical recovery, or neonatal wards of a hospital. These wards typically have patient rooms full of equipment and obstacles. It is often necessary to take X-ray exposures during the night or early morning, when ward and/or patient room lights are out. The combination of these two factors can make it very difficult for the operator to safely and un-obtrusively position the mobile X-ray device.

For the reasons stated above, and for other reasons stated below which will become apparent to those skilled in the art upon reading and understanding the present specification, there is a need in the art for adaptive lighting in mobile X-ray imaging system. There is also a need for improved lighting that conveys information and does not interfere with the lighting of the room where the X-ray system is being used.

BRIEF DESCRIPTION OF THE INVENTION

The above-mentioned shortcomings, disadvantages and problems are addressed herein, which will be understood by reading and studying the following specification.

In one aspect, an illumination apparatus for a mobile imaging system is disclosed employing an adjustable light source and device for driving the adjustable light source upon the acquisition of a triggering signal. The light source can be used to provide status indication, pathway illumination, and/or creation of favorable lighting environment.

In another aspect, the light source is one or more red light emitting diode (LED), green light emitting diode (LED), blue light emitting diode (LED), incandescent bulb, collimator lamp, halogen lamp, fluorescent lamp, organic display, or any other light-emitting technology.

In yet another aspect, the triggering signal is one or more movement of the Mobile imaging system, operational status of the Mobile imaging system, ambient light detection, and switch activation. The ambient light detection is a photosensor generated signal based on received light signals at the Mobile imaging system.

In still another aspect, a mobile imaging system having a mobile X-ray unit base, a column operably coupled to the mobile X-ray unit base, a horizontal arm operably coupled to the column, an X-ray source operably coupled to the horizontal arm, a processor operably coupled to the X-ray source, an X-ray detector operably coupled to the processor; and software means operative on the processor for: receiving a triggering signal and for selecting an illumination arrangement based on the acquired triggering signal.

In a further aspect, a method for illuminating a mobile imaging system by providing an adjustable light source operable to emit light for status indication, pathway illumination, and/or creation of favorable lighting environment and driving the lighting source based on an acquired triggering signal.

Systems, methods and apparatus are provided through which in some embodiments a lighting source, in a mobile imaging system, having one or more light generator is configured to emit light at one or more wavelength in response to a triggering signal. A photosensor is arranged to receive light at the mobile imaging system, and a control system is configured to sample an output signal of the photosensor and adjust the triggering signal responsive thereto to thereby adjust the light being emitted by the light source. The controller is also configured to generate a control signal based on the status of the mobile imaging system such as "ON" or "OFF", on the movement of the mobile imaging system to illuminate the path, and on the user's preference.

Apparatus, systems, and methods of varying scope are described herein. In addition to the aspects and advantages described in this summary, further aspects and advantages will become apparent by reference to the drawings and by reading the detailed description that follows.

DETAILED DESCRIPTION OF THE INVENTION

In the following detailed description, reference is made to the accompanying drawings that form a part hereof, and in which is shown by way of illustration specific embodiments which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

Figure 1:
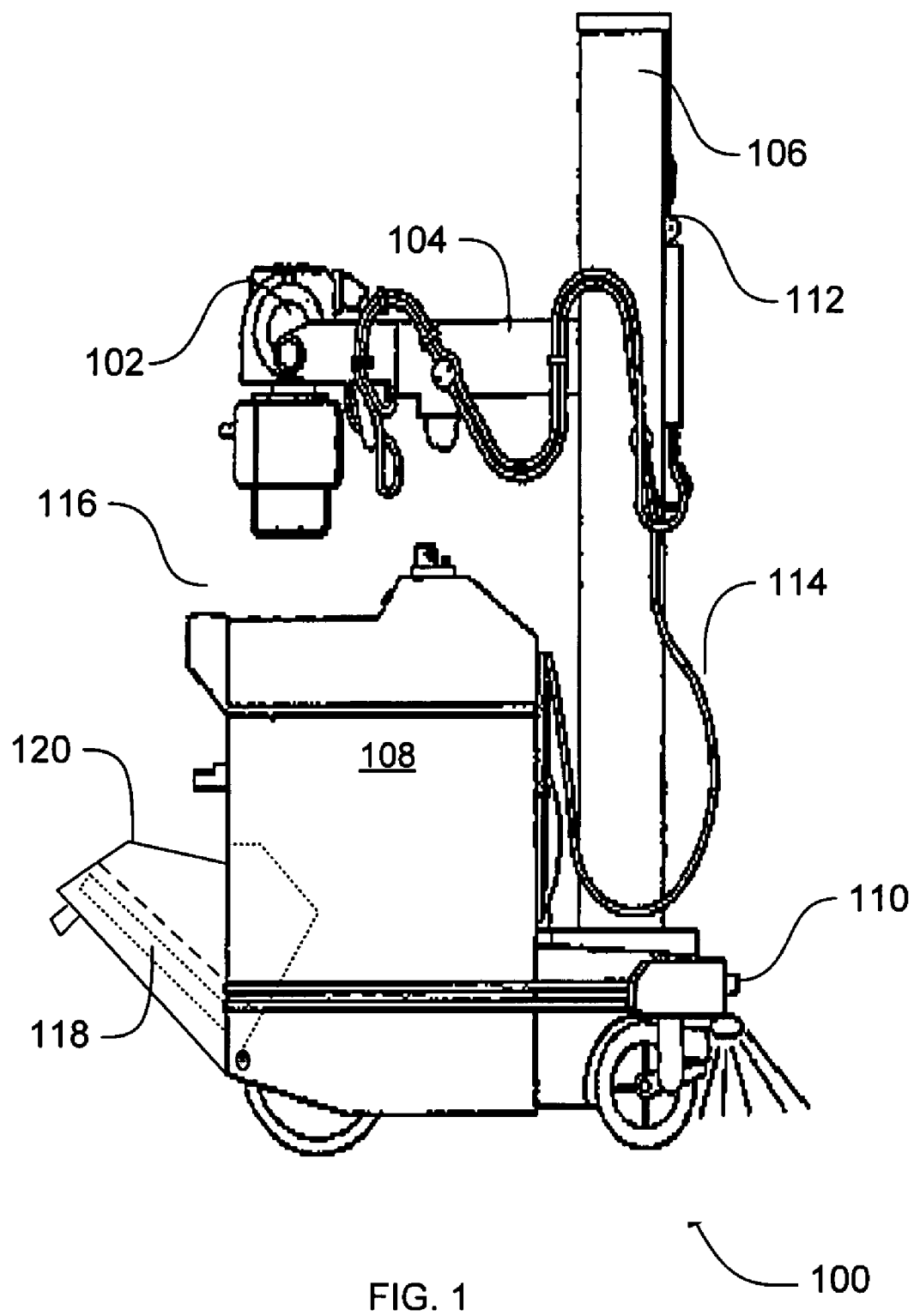
FIG. 1 is a diagram illustrating a system-level overview of an embodiment.

FIG. 1 is a cross section block diagram of an overview of a system to mobile imaging system. Mobile imaging system 100 solves the need in the art for adaptive lighting in mobile X-ray imaging system.

Mobile imaging system 100 includes an X-ray source 102 mounted at the end of horizontal arm 104. The X-ray source 102 is positionable over the object or region of interest to be imaged. The X-ray source 102 is typically mounted through a gimbal type arrangement in which a column 106 is required to rotate to move the X-ray source 102 from the park position on the mobile base unit 108 to the appropriate position in order to take an X-ray image of a patient. The X-ray source assembly 102 includes an X-ray tube housing containing an X-ray source, the tube housing having an X-ray emission aperture (not shown), and a collimator attached to the tube housing and aligned with the X-ray emission aperture. The mobile imaging system 100 further includes an imaging computer (not shown) described in FIG. 2 and a removable X-ray detector 118 in communication with a controller (not shown) through cable 114 or wireless connection (not shown). The operator of the mobile imaging system 100 is provided with a console 116 having a display or an operator interface for communicating with an imaging computer and for directing the imaging process. While it is preferred that the detector be affixable to the collimator housing, it is appreciated that the detector can be mounted in a variety of positions on the mobile X-ray system 100. It is further recognized that other detectors and numerous numbers thereof, in addition to a digital detector, are operative herein. These additional detectors may be optical in nature, or be based on other principles such as magnetic interactions, ultrasound, or inertial navigation. The mobile imaging system 100 further includes a retractable storage bin 120 for storage of an X-ray detector 118 within mobile base unit 108. The storage bin 120 may also be constructed to regulate the temperature of the stored X-ray detector 118 using passive as well as active thermal control techniques. While only a single stored X-ray detector 118 is shown, it is contemplated that the storage bin may be sized to hold multiple X-ray detectors. Further, the storage bin 120 snuggly receives each X-ray detector 118 to limit movement, vibration, stresses, and the like on the stored X-ray detector 118 when the mobile imaging system 100 is being transported. In this regard, the storage bin 120 may include deformable material such as foam to receive an X-ray detector 118 in a tightly fashion as well dampen any force that may otherwise be placed on a stored detector when the mobile imaging system is subjected to agitation.

Mobile X-ray system 100 also includes lighting sources 110 and 112, as shown positioned on column 106, that can be powered to emit a light beam based on different conditions. The light emitted by light source 110 or 112 can be manipulated or adjusted to emit a particular intensity and color. When light source 110 receives the appropriate energy in terms of voltage or current it emits the appropriate light for the desired condition. It should be noted that the lighting source could be positioned anywhere on the mobile digital X-ray imaging system 100 without departing form the intent of the invention. Additionally, the lighting panel could have a single lighting source (110 or 112), or plural light sources all combinable to produce a desired illumination arrangement.

In the previous section, a system level overview of the operation of an embodiment was described. In this section, the particular apparatus of such an embodiment are described by reference to a series of diagrams.

Figure 2:
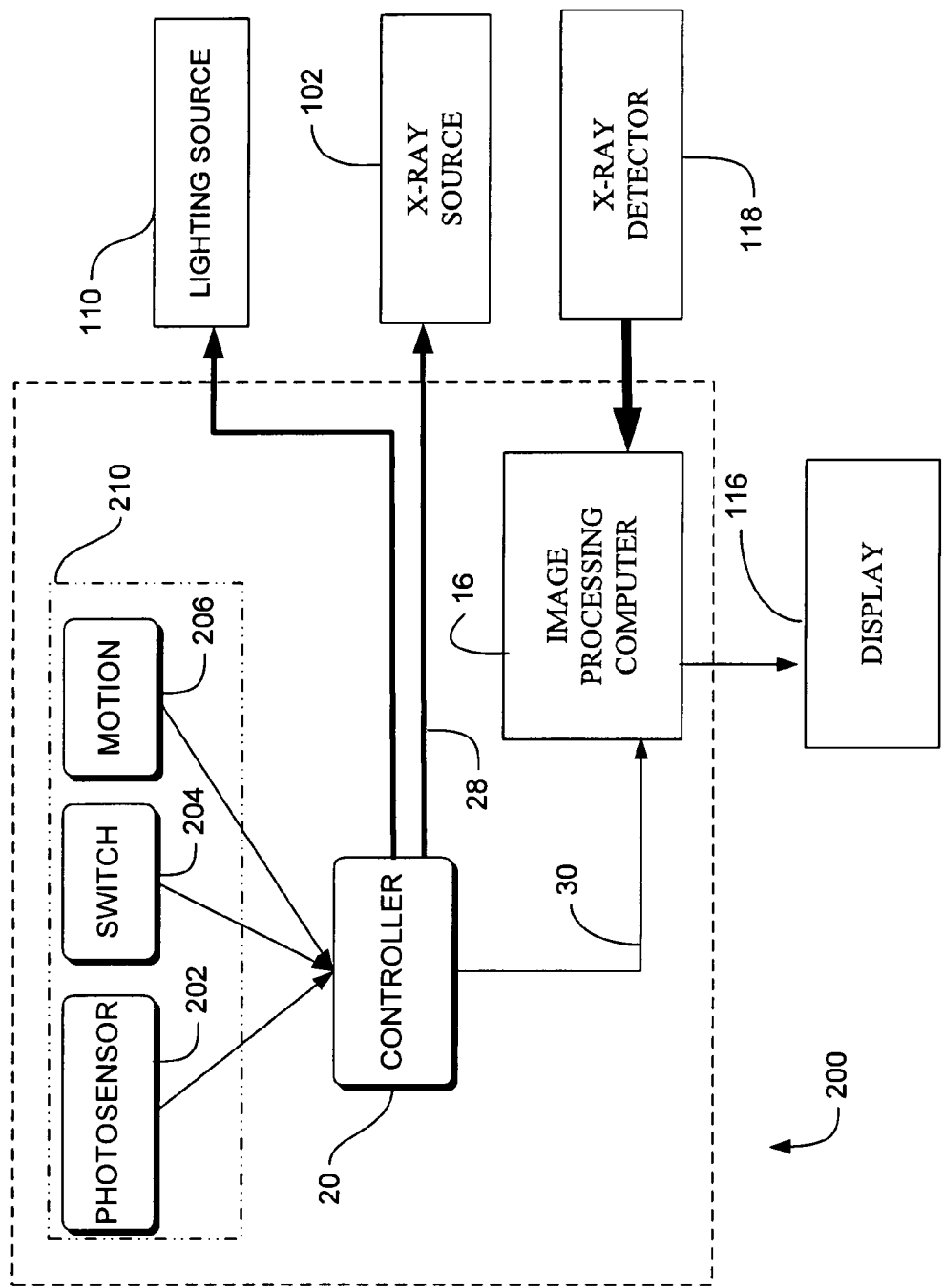
FIG. 2 is a block diagram of a hardware and operating environment in which different embodiments can be practiced.

FIG. 2 is a block diagram of apparatus 200 for controlling light source 110 according to an embodiment. Apparatus 200 includes logic (not shown) for determining the identification and the calibration of the X-ray detector 118. Additionally, apparatus 200 may include a plurality of network adapters (not shown) for exchanging data and information. The network adapters are Ethernet network adapters allowing the mobile imaging system 100 to exchange files, to share resources, and to propagate calibration data. The network adapters can be Ethernet, LocalTalk developed by Apple Computer, Inc., token ring protocol developed by IBM, fiber distributed data interface (FDDI), and asynchronous transfer mode (ATM). In addition, any conventional network topology can be used, such as linear bus, star, tree, star-wired ring or dual ring. Apparatus 200 provides a system level overview of a controlling system for illuminating an area through lighting source 110. The light source 110 is adjusted to emit a desired intensity or a desired color. Embodiments are described as operating in a multi-processing, multi-threaded operating environment on a computer.

The apparatus 200 is electrically connected to an X-ray source 102, X-ray detector 118, triggering device 210, and lighting source 110. A controller 20 within apparatus 200 communicates directly with a lighting source 102, image processing computer 16, video subsystem (not shown), and input/output devices (not shown), and X-ray source 102 and detector 118. The image processing computer 16 communicates with a display 116 and other data processing devices. During the imaging process, mobile imaging system 100 employs the X-ray source 102 mounted to one side and the X-ray detector 118 mounted to the opposed side. Further, during the imaging process the X-ray source 102 and the X-ray detector 118 are moved relative to one another in several directions along multiple image acquisition paths such as an orbital tracking direction, longitudinal tracking direction, lateral tracking direction, transverse tracking direction, pivotal tracking direction, and wig-wag tracking direction.

The imaging sequence or command to conduct the imaging process is routed to the controller 20 through dedicated input lines or wireless connections. The controller 20 sends control or trigger commands 28 to the X-ray source 102 that in turn causes one or more exposures to be taken by the X-ray detector 118. The controller 20 provides exposure reference data to the image processing computer 16. The control or trigger commands 28 and exposure reference data 30 are generated by the controller 20 based on the tracking component coordinates 26 as the imaging apparatus is moved along an image acquisition path. By way of example, the imaging apparatus 12 may be manually moved between a first and second positions (P1, P2) as a series of exposures are obtained. The image acquisition path may be along an orbital rotation direction and the X-ray detector 118 may be rotated through a range of motion from zero (0) to 145 degrees or from 0 to 190 degrees.

The image processing computer 16 collects a series of image exposures from the X-ray detector 118. The X-ray detector 118 collects an image exposure each time the X-ray source 102 is triggered by the controller 20. The image processing computer 16 combines each image exposure with corresponding exposure reference data and uses the exposure reference data to construct a three-dimensional volumetric data set. The three-dimensional volumetric data set is used to generate images, such as slices, of a region of interest from the patient. For instance, the image processor 16 may produce a display 116 from the volumetric data set saggital, coronal and/or axial views of a patient heart, lungs, veins, spine, knee, and the like.

The triggering unit 210 monitors the state of activation switch 204, acquisition of signals from a photosensor 202, and acquisition of signals from a motion sensor 206, and acquisition of internal signals that indicate the status of the X-ray source 102 or status of the X-ray detector 118 such as "ON", "OFF", or "STANDBY". The photosensor 202 signal can be coupled with other information to determine the time of day. The status of the activation switch 204 may include a signal that is indicative of activation, change in pressure when equipped with a pressure sensor, change in capacitance or in induction or electrical parameter, user command from console 116, time of day signal, or a system cue or any other form of information that is indicative of an actuation of activation switch 204.

Figure 3:
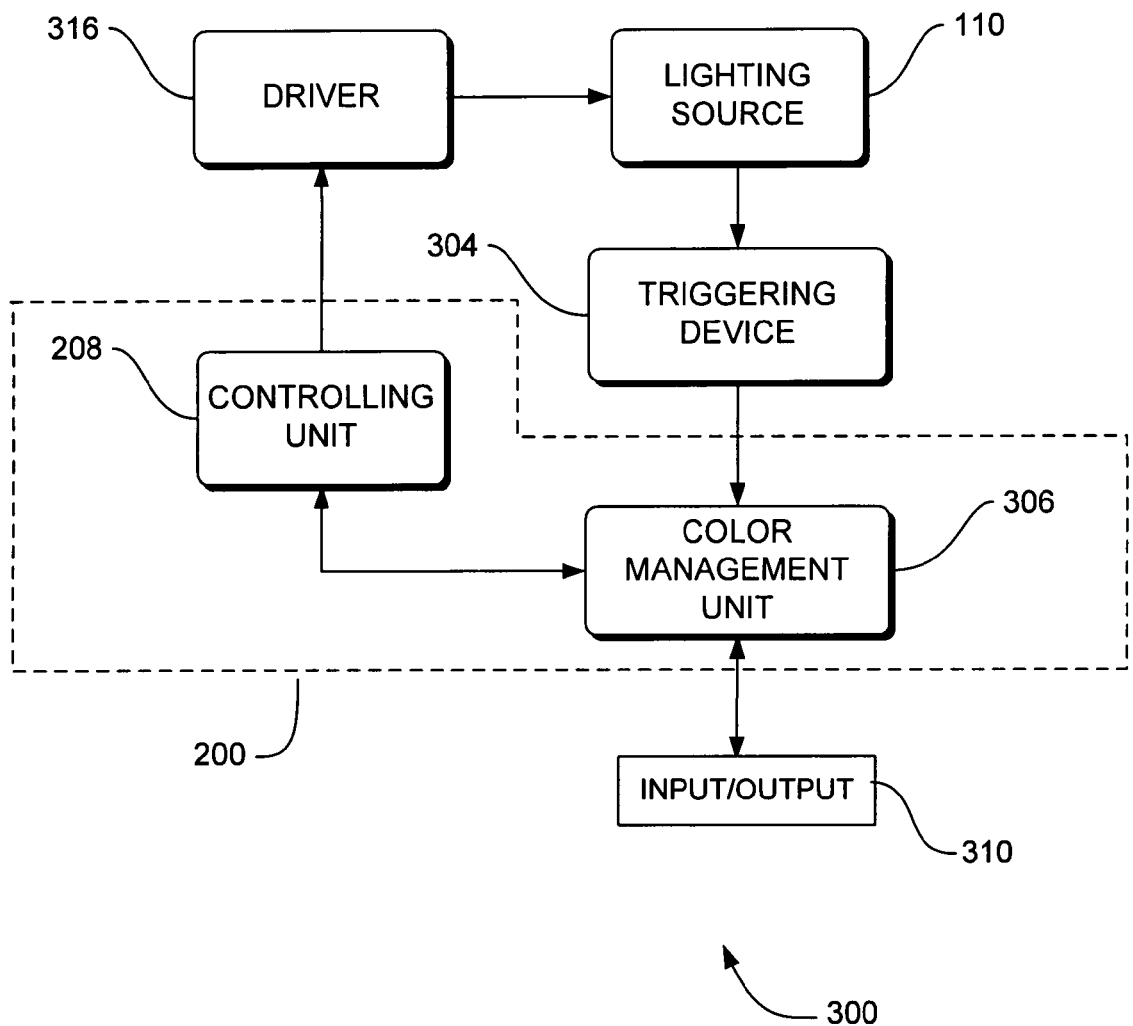
FIG. 3 is a block diagram of a control unit for controlling a lighting panel in accordance to an embodiment.

FIG. 3 illustrates an exemplary diagram of an illumination device 300 for a mobile imaging system. The illumination device 300 is one or more light generating source in a mobile digital X-ray imaging system for illuminating an area or areas inside, under or surrounding the mobile unit. The illumination device 300 includes a lighting source 110. The lighting source 110 may include an individual light emitting diode (LED), a plurality of LEDs assembled as tiles as shown by item 402 at FIG. 4. However, it should be noted that embodiments with lighting sources formed in other configurations and modality are contemplated such as, for example, incandescent bulbs, the existing collimator lamp of mobile imaging system 100, halogen lamps, fluorescent lamps, organic displays, or any other light-emitting technology that may generate a light.

In particular embodiments, however, a lighting source 110 includes a plurality of LEDs each having a dominant wavelength. As it is well known to those in the art the dominant wavelength is the hue of the color being emitted by the LED. Thus, a red LED has a dominant wavelength in the red region of the International Commission on Illumination (CIE) color space. An example arrangement for lightning source 110 is shown with reference to tile 402 (FIG. 4) consisting of a red LED 404, a green LED 406, a blue LED 408, and an orange LED 410. These LEDs can be combined to provide an indication of the status of the imaging process and operational status of the mobile imaging system 100 by indicating the state of a component such as X-ray detector 118 in addition to pathway illumination, and/or creating a favorable lighting environment. Examples, of mobile imaging system conditions are error, exposure inhibit, exposure, low battery, OFF, ON, STANDBY, temperature, etcetera. Driver 316 applies the appropriate energy in terms of voltage or current to light source 110.

Figure 4:
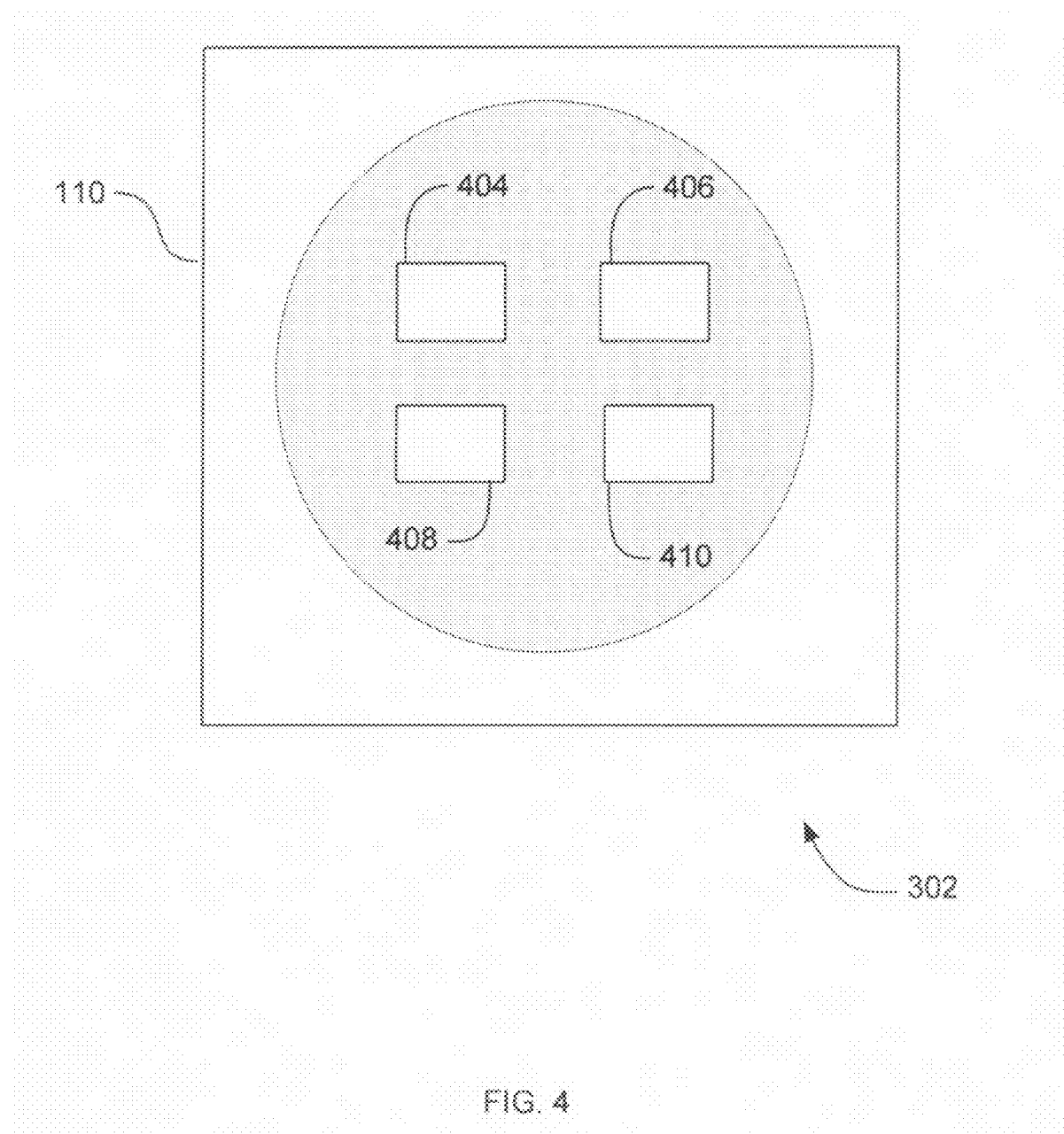
FIG. 4 is a top view of a solid state lighting device including a plurality of LEDs in accordance to an embodiment.

As an indicator, light source 110 may consist of one or more light emitting diodes (LEDs) or other lighting modality as indicated above. The light source 110 as illustrated in FIG. 4 has red LED 404, green LED 406, blue LED 408, or any other combination of LEDs. In combination, these indicators can inform the operator of the operational status of the mobile imaging system 100 such as indication that the X-ray detector 118 is shifting between states like "ON" or "OFF", state of the X-ray detector 118, and temperature and environmental conditions that may need special attention. Other examples of mobile imaging system conditions are error, exposure inhibit, exposure, low battery, OFF, ON, STANDBY, temperature, etcetera. The following table, while not comprehensive of the different permutations, combines the LEDs to convey information about X-ray detector 118. Other combinations are possible without departing from the scope of the embodiment:

| STATUS | LED404 Duty Cycle | LED406 Duty Cycle | LED408 Duty Cycle | INDICATOR |
|---|---|---|---|---|
| Detector Off State | off | off | off | Off |
| Sleep or idle mode | half | off | off | Sleep |
| Detector ON or Ready | one | off | off | On |
| Image Transfer | third | off | off | Imaging |
| Temperature Exceeded | off | one | off | Temp |

Continuing with the operation of illumination device 300 a current driver 316 provides a driving current or voltage that causes lighting source 110 to emit a light. For example, assuming an LED arrangement, driver 316 provides the appropriate energy for each LED in lighting source 110 as depicted in FIG. 4. The driver 316 provides a constant current source for each of the separate LED of the lighting source 110 under the control of controlling unit 208. In some embodiments, the controlling unit 208 may be implemented using a microcontroller which may be programmed to provide pulse width modulation (PWM) to control separate current supply blocks (not shown) within the driver 316 for the LEDs in tile 402 in FIG. 4. Pulse width information for each of the LEDs may be obtained by the controlling unit 208 from a color management unit 306 which may include a color management controller.

The color management unit 306 may be connected to the controlling unit 208 through a communication link. The color management unit 306 may be configured as a slave device while controlling unit 208 may be configured as a master device on the link. The controlling unit 208, the color management unit 306 may together form a feedback control system configured to control the light output from the lighting source 110.

The controlling unit 208 or the color management unit 306 may include a table for lighting source 110. The table is configured to store pulse width information for each of the LEDs in the mobile imaging system 100. The values in the table may be determined by an initialization/calibration process. However, the table values may be adaptively changed over time based on user input 310 and/or input from one or more sensors in triggering unit 210 coupled to the lighting source 110.

The triggering unit 210 as noted above with FIG. 2 may include one or more photosensors 202, one or more switch 204, a motion sensor that would indicate movement of the mobile imaging system 100 as noted above with reference to FIG. 2. In particular embodiments, a lighting panel 110 may include one photosensor for each LED in the lighting panel. The primary purpose of the photosensor 202 is to ascertain the amount of light in a room where the mobile imaging system 100 is going to be performing an imaging procedure. In other embodiments, each tile 402 in the lighting source 110 may include one or more photosensors.

In some embodiments, the photosensor 202 may include photo-sensitive regions that are configured to be preferentially responsive to light having different dominant wavelengths. Thus, wavelengths of light generated by different LEDs, for example a red LED and a blue LED, may generate separate outputs from the photosensor. In some embodiments, the photosensor may be configured to independently sense light having dominant wavelengths in the red, green and blue portions of the visible spectrum. The photosensor 202 may include one or more photosensitive devices, such as photodiodes.

The photosensor 202 may be arranged at various locations within the mobile imaging system 100 in order to obtain representative sample data. Further, an optical switch may be provided to switch light from different light guides which collect light from different areas of the lighting source 110 to a photosensor 202. Thus, a single photosensor 202 may be used to sequentially collect light from various locations on the lighting source 110. For example, a single photosensor 202 is provided in the lighting panel 110. The photosensor 202 may be provided at a location where it may receive ample sample of light being emitted or being received at X-ray system 100. In order to provide more extensive data regarding light output characteristics of the lighting panel 110, more than one photosensor 202 may be used. The user input 310 may be configured to permit a user to selectively adjust attributes of the lighting source 110, such as color temperature, brightness, hue, etc.

The lighting source 110 can be combined to suit the desired lighting arrangement. The lighting panel could be used to illuminate objects in the path of the mobile imaging system 100, to power only certain light sources so as not to disrupt the circadian rhythm of the patient being imaged or other individuals in the room, to conserve power when entering a lighted room, and to provide a favorable environment by dynamically adjusting the red, green, blue color mix in reaction to ambient light detection. The following table illustrates possible scenarios that can be programmed into controlling unit 208 to meet the desired lighting arrangement.

|  | INDI-CATOR | HEAD-LIGHT | COLLIMATOR LIGHT | CONSOLE LIGHTS |
| --- | --- | --- | --- | --- |
| TRANSIT | OFF | ON | OFF | LIMITED |
| IMAGING PROCEDURE | ON | OFF | ON | ON |
| PARKED MOBILE UNIT | OFF | OFF | OFF | OFF |
| TRANSIT LIGHTED ROOM | OFF | OFF | OFF | LIMITED |
| PROCEDURE DARKENED ROOM | ON | OFF | ON | OFF |

FIG. 4 illustrates tile 402 having four LEDs 404-410 to achieve a desired emission pattern, color and/or intensity. The tile forms a compact solid state lighting source 110 that may include, for example, organic and/or inorganic light emitting devices. A solid state lighting element may comprise a packaged discrete electronic component including a carrier substrate on which a plurality of LED chips 404-410 is mounted. In other embodiments, one or more solid state lighting elements may comprise LED chips 404-410 mounted directly onto electrical traces on the surface of the tile 402, forming a multi-chip module or chip on board assembly. The LED chip may include at least a red LED 404, a green LED 406 and a blue LED 408. The lighting device 402 may include an additional orange LED 410.

Figure 5:
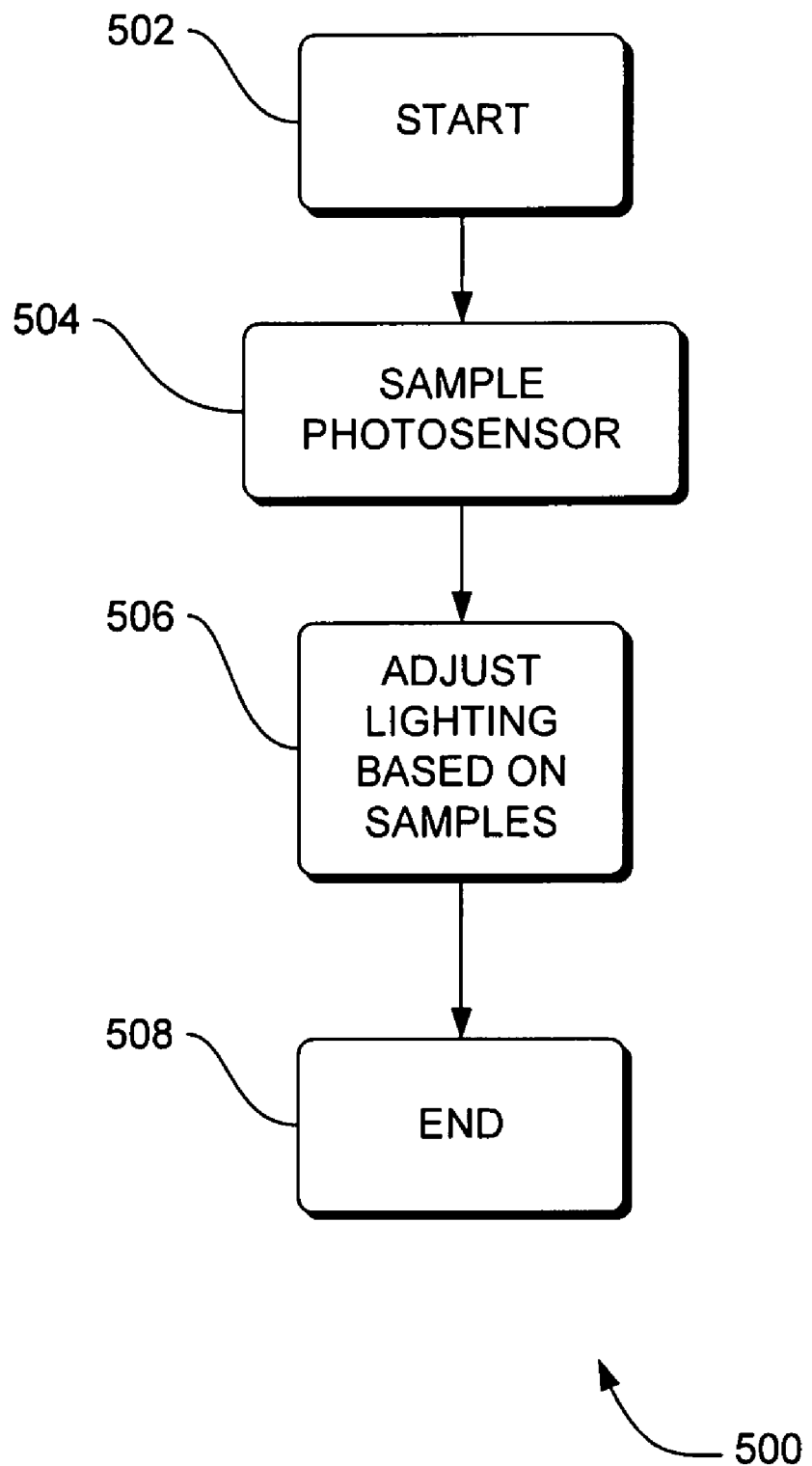
FIG. 5 is a flowchart of a method for adaptively changing lighting output according to an embodiment.

FIG. 5 is flowchart of a method 500 for adaptively adjusting the lighting of a mobile imaging system 100 in accordance to an embodiment. In particular method 500 uses photosensor 202 signals to manage the lighting source 110 to provide status indication, pathway illumination, or creation of a favorable lighting environment.

Method 500 begins with action 502 which starts the process. The process could be started by a switch such as a keyboard command at console 116, externally from another device such as from portable detector 118, or from an internal signal or timer at controller 20 in FIG. 2. Regardless of the origin, a start signifies a request to begin a process of adjusting the lighting of mobile imaging system 100. After action 502 control passes to action 504 for further processing.

In action 504 the photosensor is sampled to determine the value of light impinging on the mobile imaging system 100. The sample value may be a single value or an average of values within a given time interval. The value represents a brightness or intensity level of the light sources in the vicinity of the mobile imaging system 100. Once the value has been ascertained control passes to action 506 for further processing.

In action 506, the lighting is adjusted based on the acquired samples. In action 506, certain lighting sources are turned "ON" or "OFF" based on the desired lighting affects. The desired amount of red, green, blue, and orange can be achieved by the operator and the color management unit in unison with controlling unit 208. The color management unit 306 is able to samples the light output from the RGB LED array (402-410), processes the color information and adjusts the light output from the RGB LEDs until the target color is achieved. To achieve this, the device integrates an RGB photo sensor array, an analog-to-digital converter (not shown) front-end, a color data processing logic core and a high-resolution 12-bit PWM output generator.

In action 508, the method is terminated until it is called again by the system to adaptively adjust the lighting.

Figure 6:
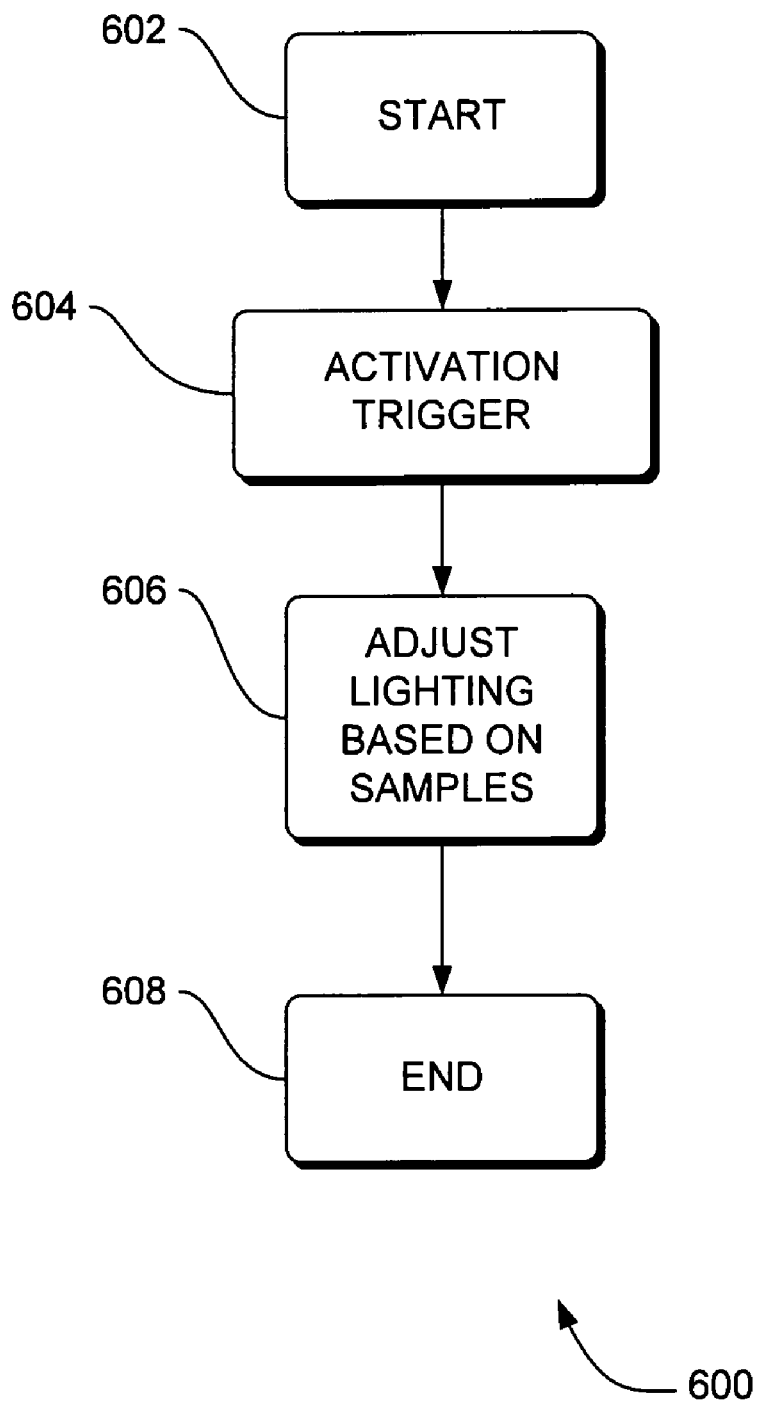
FIG. 6 is a flowchart of a method for adaptively changing lighting output according to an embodiment.

FIG. 6 is flowchart of a method 600 for adaptively adjusting the lighting of a mobile imaging system in accordance to an embodiment. In particular method 600 uses an activation signal to manage the lighting source 110 so as to provide status indication, pathway illumination, or creation of a favorable lighting environment.

Method 600 begins with action 602 which starts the process. The process could be started by a switch such as a keyboard command at console 116, externally from another device such as X-ray detector 118, from an internal signal or timer at mobile imaging system 100 such as motion switch 206, or from switch 204. Regardless of the origin of the command or the signal a start signifies a request to begin a process of adjusting the lighting of mobile imaging system 100. After start 602 control passes to action 604 for further processing.

In action 604, is determination is made if an activation trigger has been received by the system. The activation trigger can be a switch 204 toggled by an operator, time of day signal, a signal from the portable X-ray detector 118 indicating that it is image capable, a signal from the mobile imaging system 100 that the imaging process has been started or has been terminated, or a user command through console 116.

In action 606, the appropriate energy on terms of current or voltage is applied light source 110 based on the acquired samples. In action 606, the color and intensity of certain lighting sources are adjusted based on the desired lighting affects.

In action 608, the method is terminated until it is called again by the system to adaptively adjust the lighting.

Figure 7:
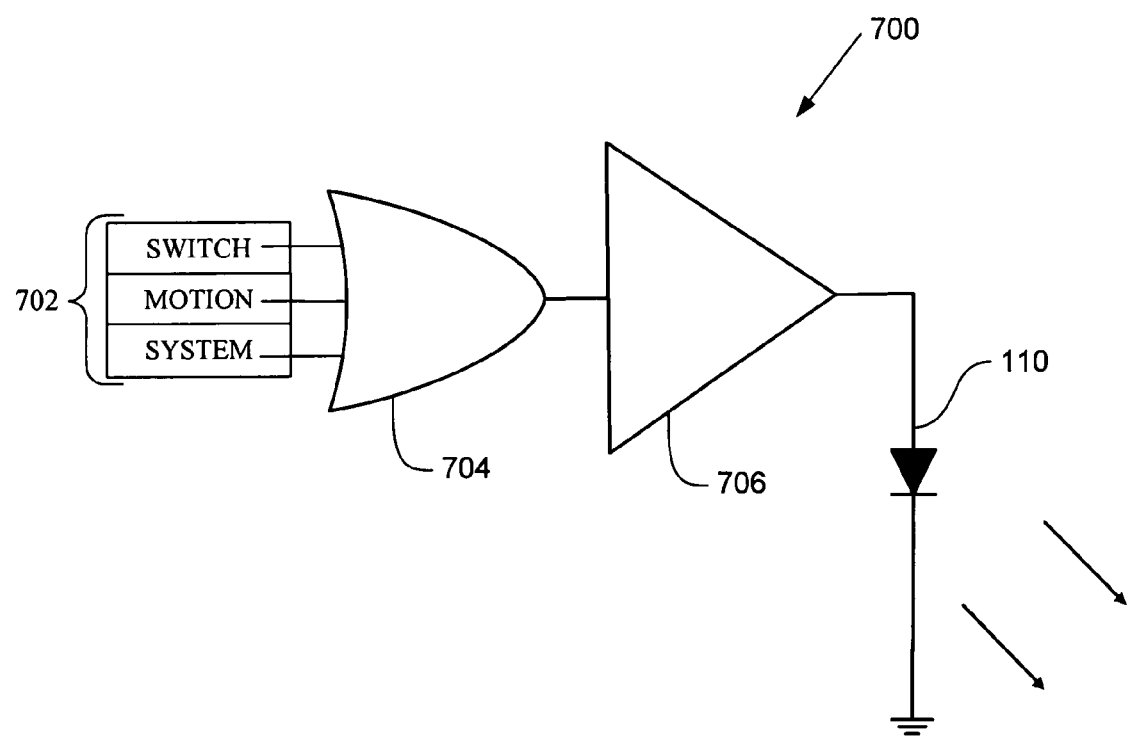
FIG. 7 is a block diagram of an apparatus for illuminating a mobile imaging system according to an embodiment.

FIG. 7 is a block diagram for illumination apparatus 700 for use with a mobile imaging system having as set of triggering signal 702 or triggering event, a driver 706 for generating a driving signal in response to triggering signals that causes light source 110 to emit a light. As noted earlier light source 110 is one or more light emitting diode (LED) or any other suitable light source. Logic gate 704 is particularly useful for programming when activation of the power driver/switch 706 should occur. The activation occurs at set triggering events and with corresponding "on" and "off." states when the trigger event is put in its "on" state, the logic gate 704 goes to the "on" state and electric energy flows through the power driver/switch unit 706. When the trigger event is put in its "off" state, the logic gate 704 goes to the "off" state. The triggering event are from photosensor 202, switch 204, motion sensor 206 or other user defined parameter(s) either measured or derived from other parameters. An example of a user defined triggering event is time of day that can be based from photosensor 202 signals or from user and system commands. The logic gate 704 switches the state of the power driver/switch 706 and the light source 110 in order to achieve the desired lighting effect. The power driver/switch 706 applies the appropriate energy in terms of voltage or current to light source 110.

CONCLUSION

A method and system have been described. A technical effect of the method and system is to dynamically adjust the lighting in a mobile imaging system such mobile imaging system 100 in FIG. 1. Although specific embodiments are illustrated and described herein, it will be appreciated by those of ordinary skill in the art that any arrangement which is calculated to achieve the same purpose may be substituted for the specific embodiments shown. This application is intended to cover any adaptations or variations.

In particular, one of skill in the art will readily appreciate that the names of the methods and apparatus are not intended to limit embodiments. Furthermore, additional methods and apparatus can be added to the components, functions can be rearranged among the components, and new components to correspond to future enhancements and physical devices used in embodiments can be introduced without departing from the scope of embodiments. One of skill in the art will readily recognize that embodiments are applicable to future mobile digital X-ray imaging systems, different X-ray imaging systems, and new imaging system that require dynamic lighting arrangements.

We claim:

1. A mobile imaging system comprising:
a base of the mobile imaging system having wheels;
a light source mounted on the base of the mobile imaging system and operable to emit light for pathway illumination;
at least one device mounted on the mobile imaging system and operable to acquire at least one triggering signal; and
a driver in the mobile imaging system and operable to drive the lighting source based on the at least one acquired triggering signal,
wherein the driver communicates directly with the light source and the at least one device operable to acquire the at least one acquired triggering signal.

2. The mobile imaging system of claim 1, wherein the light source is adjustable as to color and intensity.

3. The mobile imaging system of claim 1, wherein the light source further comprises:
at least one of red light emitting diode (LED), green LED, blue LED, incandescent bulb, collimator lamp, halogen lamp, fluorescent lamp, organic display, or any other light-emitting technology.

4. The mobile imaging system of claim 1, wherein the at least one triggering signal further comprises:
at least one of movement of the mobile imaging system, operational status of the mobile imaging system, ambient light detection, time of day, and a command.

5. The mobile imaging system of claim 4, wherein the at least one triggering signal further comprises:
an operational status of the mobile imaging system; and
the operational status of the mobile imaging system further comprises:
an indication of mobile imaging system condition, status or event.

6. The mobile imaging system of claim 4, wherein the at least one at least one device operable to acquire at least one triggering signal further comprises:
a photosensor and wherein the at least one triggering signal further comprises the ambient light detection and the ambient light detection is a photosensor generated signal based on received light signals at the mobile imaging system.

7. The mobile imaging system of claim 1, wherein the driver selects the light source and intensity of the light source in response to the acquired at least one triggering signal.

8. A mobile imaging system comprising:
a mobile unit base;
a column operably coupled to the mobile unit base;
a horizontal arm operably coupled to the column;
an X-ray source operably coupled to the horizontal arm;
a controller operably coupled to the X-ray source;
a lighting panel operably coupled to the controller, the lighting panel mounted on the mobile unit base operably coupled to the controller and the lighting panel facing down to provide pathway illumination;
an X-ray detector operably coupled to the controller; and
the controller configured for:
receiving at least one triggering signal wherein the at least one triggering signal indicates movement of the mobile imaging system; and
selecting an illumination arrangement based on the acquired triggering signal;
wherein the controller communicates directly with the lighting panel, the X-ray source and X-ray detector.

9. The system of claim 8, wherein the light source is adjustable as to color and intensity.

10. The system of claim 8, wherein the light source further comprises:
at least one of red light emitting diode (LED), green LED, blue LED, incandescent bulb, collimator lamp, halogen lamp, fluorescent lamp, organic display, or any other light-emitting technology.

11. The system of claim 8, wherein the at least one triggering signal further comprises:
an indication of at least one of operational status of the mobile imaging system, ambient light detection, time of day and user command.

12. The system of claim 11, wherein the at least one triggering signal further comprises:
an operational status of the mobile imaging system and the operational status of the mobile imaging system further comprises an indication of mobile imaging system condition, status or event.

13. The system of claim 11, wherein the at least one device operable to acquire the at least one triggering signal is acquired by a photosensor, the photosensor being arranged to generate a signal based on received light signals at the mobile imaging system and wherein the at least one triggering signal further comprises the ambient light detection and the ambient light detection is from the photosensor.

14. The system of claim 8, wherein the controller selects the light source and the intensity of the selected light source in response to the acquired at least one triggering signal.

15. A method for illuminating a mobile imaging system, the method comprising:
providing a light source on a base of the mobile imaging system which is operable to emit light for pathway illumination;
generating at least one trigger command and exposure reference data based on tracking coordinates as an X-ray source of the mobile imaging system is moved along an image acquisition path;
providing the at least one trigger command to the X-ray source of the mobile imaging system;
providing the exposure reference data to an image processing computer;

acquiring a triggering signal, wherein the triggering signal further comprises an indication of movement of the mobile imaging system; and driving the lighting source based on the acquired triggering signal.

16. The method of claim 15, wherein the light source is adjustable as to color and intensity.

17. The method of claim 15, wherein the light source further comprises:

at least one of red light emitting diode (LED), green LED, blue LED, incandescent bulb, collimator lamp, halogen lamp, fluorescent lamp, organic display, or any other light-emitting technology.

18. The method of claim 15, wherein the triggering signal further comprises:

at least one of operational status of the mobile imaging system, ambient light detection, time of day, and a command.

19. The method of claim 18, wherein the triggering signal further comprises:

an operational status of the mobile imaging system and the operational status of the mobile imaging system further comprises an indication of mobile imaging system condition status, or event.

20. The method of claim 18, wherein the triggering signal further comprises:

the ambient light detection and the ambient light detection is from a photosensor arranged to generate a signal based on received light signals at the mobile imaging system.

21. The method of claim 15, wherein driving the lighting source further comprises:

selecting the light source and the intensity of the light source in response to the acquired triggering signal.

22. The method of claim 15, wherein driving the lighting source further comprises:

applying an appropriate energy to the lighting source.

* * * * *